(12) United States Patent
Darteil et al.

(10) Patent No.: US 11,371,098 B2
(45) Date of Patent: Jun. 28, 2022

(54) METHODS FOR DIAGNOSING AND EVALUATING NON-ALCOHOLIC STEATOHEPATITIS

(71) Applicant: Genfit, Loos (FR)

(72) Inventors: Raphaël Darteil, Villeurbanne (FR); Geneviève Cordonnier, Templemars (FR); John Brozek, Saint-Amand-les-Eaux (FR); Emilie Praca, Lille (FR); Fouad Ben Sudrik, Lille (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 15/759,484

(22) PCT Filed: Sep. 14, 2016

(86) PCT No.: PCT/EP2016/071727
§ 371 (c)(1),
(2) Date: Mar. 12, 2018

(87) PCT Pub. No.: WO2017/046181
PCT Pub. Date: Mar. 23, 2017

(65) Prior Publication Data
US 2018/0265924 A1     Sep. 20, 2018

(30) Foreign Application Priority Data
Sep. 14, 2015   (EP) .................... 15306412

(51) Int. Cl.
| | | |
|---|---|---|
| *C12Q 1/6883* | (2018.01) |
| *A61P 1/16* | (2006.01) |
| *A61K 31/192* | (2006.01) |
| *G01N 33/66* | (2006.01) |
| *G01N 33/72* | (2006.01) |
| *G01N 33/68* | (2006.01) |

(52) U.S. Cl.
CPC .......... *C12Q 1/6883* (2013.01); *A61K 31/192* (2013.01); *A61P 1/16* (2018.01); *G01N 33/66* (2013.01); *G01N 33/6893* (2013.01); *G01N 33/723* (2013.01); *C12Q 2600/158* (2013.01); *C12Q 2600/178* (2013.01); *G01N 2333/78* (2013.01); *G01N 2333/8107* (2013.01); *G01N 2800/085* (2013.01); *G01N 2800/52* (2013.01)

(58) Field of Classification Search
CPC ........ C12Q 1/6883; A61P 1/16; A61P 31/192; G01N 33/66; G01N 33/6893; G01N 33/723
See application file for complete search history.

(56) References Cited

U.S. PATENT DOCUMENTS

2012/0252725 A1* 10/2012 Darteil ................ A61K 31/155
514/6.5

FOREIGN PATENT DOCUMENTS

| CN | 104293908 A | 1/2015 |
| KR | 20140147920 A | 12/2014 |
| WO | WO 2013/068348 A1 | 5/2013 |
| WO | WO 2014/049131 A1 | 4/2014 |

OTHER PUBLICATIONS

Priya et al., A preliminary study of inflammatory markers in non-alcoholic steatohepatitis, Libyan J Med 2010, 5: 5071.*
Feng et al., "Aberrant hepatic microRNA expression in nonalcoholic fatty liver disease," Cell Physiol Biochem, 2104; 34(6): 1983-97.*
Cermelli et al., "Circulating MicroRNAs in Patients with Chronic Hepatitis C and Non-Alcoholic Fatty Liver Disease," Aug. 2011, vol. 6, Issue 8.*
Sanal, "Biomarkers in nonalcoholic fatty liver disease—the emperor has no clothes," Mar. 21, 2015, 21(11):3223-3231.*
Feng et al., "Aberrant Hepatic MicroRNA Expression in Nonalcoholic Fatty Liver Disease," Cell Physiol Biochem 2014;34:1983-1997.*
Enomoto et al., "Liver fibrosis markers of nonalcoholic steatohepatitis," World J Gastroenterol Jun. 28, 2015.*
Tanwar et al., "Validation of terminal peptide of procollagen III for the detection and assessment of nonalcoholic steatohepatitis in patients with nonalcoholic fatty liver disease," Hepatology Jan. 2013; 57(1):103-11.*
Motawi et al., "Serum MicroRNAs as Potential Biomarkers for Early Diagnosis of Hepatitis C Virus-Related Hepatocellular Carcinoma in Egyptian Patients," PLOS One Sep. 9, 2015.*
Rius et al., "Resolvin D1 primes the resolution process initiated by calorie restriction in obesity-induced steatohepatitis," The FASEB Journal, vol. 28, Feb. 2014.*
Clarke et al., Circulating microRNA 122 in the methionine and choline-deficient mouse model of non-alcoholic steatohepatitis. J Appl Toxicol. Jun. 2014;34(6):726-32. doi: 10.1002/jat.2960. Epub Nov. 12, 2013.
Tryndyak et al., Plasma microRNAs are sensitive indicators of inter-strain differences in the severity of liver injury induced in mice by a choline- and folate-deficient diet. Toxicol Appl Pharmacol. Jul. 1, 2012;262(1):52-9. doi:10.1016/j.taap.2012.04.018. Epub Apr. 24, 2012.

(Continued)

Primary Examiner — Jared Barsky
(74) Attorney, Agent, or Firm — McDermott Will & Emery LLP (57) ABSTRACT

The invention relates to a method for the diagnosis of non-alcoholic steatohepatitis (NASH), for determining the activity, the stage, or the severity of NASH or for classifying a subject as a potential receiver or non receiver of a treatment of NASH using circulating miRNAs and other blood circulating markers of liver damage, e.g. alpha 2 macroglobulin, HbA1c, N-terminal pro-peptide of collagen type III, miR-34 and miR-200. It also relates to a kit for implementing the method of the invention, and the compounds for use in a method for the treatment of NASH, wherein the subject to be treated is identified, evaluated or classified according to the method of the invention.

2 Claims, 1 Drawing Sheet
Specification includes a Sequence Listing.

(56) References Cited

OTHER PUBLICATIONS

Yamada et al., Associations between circulating microRNAs (miR-21, miR-34a, miR-122 and miR-451) and non-alcoholic fatty liver. Clin Chim Acta. Sep. 23, 2013;424:99-103. doi: 10.1016/j.cca.2013.05.021. Epub May 30, 2013.

* cited by examiner

METHODS FOR DIAGNOSING AND EVALUATING NON-ALCOHOLIC STEATOHEPATITIS

RELATED APPLICATIONS

This application is a national stage filing under 35 U.S.C. § 371 of international application number PCT/EP2016/071727, filed Sep. 14, 2016, which claims priority to EP application number 15306412.6, filed Sep. 14, 2015, the entire disclosure of each of which is incorporated by reference herein in its entirety.

FIELD OF THE INVENTION

The invention relates to a method for the diagnosis of non-alcoholic steatohepatitis (NASH), for determining the activity, the stage, or the severity of NASH or for classifying a subject as a potential receiver or non receiver of a treatment of NASH. It also relates to a kit for implementing the method of the invention, and the compounds for use in a method for the treatment of NASH, wherein the subject to be treated is identified, evaluated or classified according to the method of the invention.

BACKGROUND OF THE INVENTION

Non-alcoholic steatohepatitis (NASH) is a progressive disease of the liver characterized histologically by fatty acid accumulation, hepatocyte damage and inflammation resembling alcoholic hepatitis. NASH is a critical stage in the process that spans from hepatic steatosis to cirrhosis and liver failure. A careful history of a lack of significant alcohol intake is essential to establish this diagnostic. NASH is one of the most common causes of elevated aminotransferases in patients referred for evaluation to hepatologists. Obesity and type-2 diabetes are associated to NASH. Since the prevalence of these diseases is increasing, the prevalence of NASH is also expected to increase and therefore, this disease is becoming an emerging public issue in the United States as well as in other countries.

Although several attempts have been made to propose non-invasive methods for diagnosing and determining the activity, the stage, or the severity of NASH, as of today histological analysis of liver biopsies remains the optimal approach for differentiating NASH from early stage steatosis. Steatosis, lobular and portal inflammation, hepatocyte injury in the forms of ballooning and apoptosis, and fibrosis are features of NASH evaluated from the biopsy. However, liver biopsy has a number of obvious drawbacks. First, the material collected in liver biopsy represents only a very small part of the liver of the diagnosed subject, thereby raising doubts on whether the collected sample is representative of the global state of the subject's organ. Moreover, liver biopsy is a very invasive procedure that may be cumbersome, worrisome and painful for the patient, and which raises concerns about morbidity and mortality. At last, in view of the foregoing, liver biopsy cannot be reasonably proposed as a routine procedure for determining whether a person in the general population, or even patients at risk of NASH, suffers from NASH and/or for determining the activity, the stage, or the severity of NASH in said person.

Therefore, a strong need exists in providing accurate, non-invasive, means for diagnosing and determining the activity, the stage, or the severity of NASH in a subject.

SUMMARY OF THE INVENTION

The present invention is based on a very fine and complete analysis of a vast number of variables determined from more than 300 high quality samples obtained from NASH patients during a clinical trial conducted by the Applicant (study GFT505-212-7-NCT01694849), including histological data obtained from liver biopsies of the patients. This study led to the discovery of key circulating factors (or biomarkers) indicative of NASH and of its severity or stage or activity.

Accordingly, a first aspect of the invention relates to a method for the diagnosis of non-alcoholic steatohepatitis (NASH) or for determining the activity, the stage, or the severity of NASH in a subject, comprising the measure of the level of at least one blood, serum or plasma circulating micro-RNA marker of NASH and at least one other blood, serum or plasma circulating marker of liver damage.

Preferably, this first aspect of the invention relates to a method for the diagnosis of non-alcoholic steatohepatitis (NASH) or for determining the activity, the stage, or the severity of NASH in a subject, comprising the step of measuring the level of at least one marker selected from either group (i), (ii) or (iii), and at least one marker selected from either group (iv) or (v) defined as follows:
  (i) alpha 2 macroglobulin
  (ii) glycated haemoglobin (HbA1c), fasting glucose level, fructosamine level
  (iii) N-terminal pro-peptide of collagen type III
  (iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
  (v) hsa-miR-200 (in particular hsa-miR-200a, more particularly hsa-miR-200a-3p).

In a particular embodiment of the first aspect, the method comprises the implementation of the following measures from a blood, serum or plasma sample of said subject:
  (i) determining the level of alpha 2 macroglobulin;
  (ii) determining the level of at least one marker selected in the group consisting of HbA1c, fasting glucose level, fructosamine level;
  (iii) determining the level of N-terminal pro-peptide of collagen type III;
  (iv) determining the level of at least one marker selected in the group consisting of hsa-miR-34, hsa-miR-122 and hsa-miR-192; and
  (v) determining the level of hsa-miR-200;
wherein an increase in said levels relative to that of a control sample is indicative of NASH and/or of the activity, the stage, or the severity of NASH.

In a further embodiment of the first aspect of the invention:
  measure (ii) comprises determining the level of at least HbA1c; and/or
  measure (iv) comprises determining the level of at least hsa-miR-34.

In another aspect, the method of the first aspect comprises determining the level of alpha 2 macroglobulin, HbA1c, N-terminal pro-peptide of collagen type III, hsa-miR-34 and hsa-miR-200.

In yet another embodiment of the first aspect, a NASH score is calculated from the levels determined in measures (i) to (v) and wherein NASH is diagnosed and/or NASH stage or activity or severity is determined on the basis of said NASH score.

In another embodiment of the first aspect, the NASH score is calculated according to the following logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.

In a specific variant of this embodiment:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.

In a further embodiment of the first aspect, a NASH score higher than a threshold value comprised between 0.102 and 0.6465 is indicative of a severe NASH, or of a moderate or high NASH activity.

In a variant of this embodiment:
k is equal to 25.13;
a is equal to 0.60;
b is equal to 0.48;
c is equal to 0.1;
d is equal to −0.43; and
f is equal to −0.45;
and wherein the threshold value is comprised between 0.102 and 0.462, and is more particularly equal to 0.23.

In an alternative variant of this embodiment:
k is equal to 21.35;
a is equal to 0.62;
b is equal to 0.55;
c is equal to 0.14;
d is equal to −0.38; and
f is equal to −0.39;
and wherein the threshold value is comprised between 0.2319 and 0.6465, and is more particularly equal to 0.4343

A second aspect of the invention relates to a method for classifying a subject as a receiver or non receiver of a treatment for non-alcoholic steatohepatitis (NASH), comprising the measure of the level of at least one blood, serum or plasma circulating micro-RNA marker of NASH and at least one other blood, serum or plasma circulating marker of liver damage.

Preferably, this second aspect of the invention relates to a method for classifying a subject as a receiver or non receiver of a treatment for non-alcoholic steatohepatitis (NASH), comprising the step of measuring the level of at least one marker selected from either group (i), (ii) or (iii), and at least one marker selected from either group (iv) or (v) defined as follows:

(i) alpha 2 macroglobulin
(ii) glycated haemoglobin (HbA1c), fasting glucose level, fructosamine level
(iii) N-terminal pro-peptide of collagen type III
(iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
(v) hsa-miR-200 (in particular hsa-miR-200a, more particularly hsa-miR-200a-3p).

In a particular embodiment of the second aspect of the invention, the method comprises the implementation of the following measures from a blood, serum or plasma sample of said subject:
(i) determining the level of alpha 2 macroglobulin;
(ii) determining the level of at least one marker selected in the group consisting of HbA1c, fasting glucose level, fructosamine level;
(iii) determining the level of N-terminal pro-peptide of collagen type III;
(iv) determining the level of at least one marker selected in the group consisting of hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p); and
(v) determining the level of hsa-miR-200 (in particular hsa-miR-200a, more particularly hsa-miR-200a-3p);
wherein a NASH score is calculated from the levels determined in measures (i) to (v) and wherein the subject is classified as a receiver or non receiver of the treatment for NASH based on said score.

In a further embodiment of the second aspect:
measure (ii) comprises determining the level of at least HbA1c; and/or
measure (iv) comprises determining the level of at least hsa-miR-34 (in particular hsa-miR-34a, more particularly hsa-miR-34a-5p).

In another embodiment of the second aspect, the method comprises determining the level of alpha 2 macroglobulin, HbA1c, N-terminal pro-peptide of collagen type III, hsa-miR-34 (in particular hsa-miR-34a, more particularly hsa-miR-34a-5p) and hsa-miR-200 (in particular hsa-miR-200a, more particularly hsa-miR-200a-3p).

In yet another embodiment of the second aspect, the NASH score is calculated according to the following logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;

d is a number comprised between −0.77 and 0;
f is a number comprised between −0.78 and 0.

In a variant of this embodiment:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.

In yet another embodiment of the second aspect, the subject is classified as a receiver of the treatment if S is higher than a threshold value comprised between 0.102 and 0.6465.

In a variant of this embodiment:
k is equal to 25.13;
a is equal to 0.6;
b is equal to 0.48;
c is equal to 0.1;
d is equal to −0.43; and
f is equal to −0.45;
and wherein the threshold value is comprised between 0.102 and 0.462, and is more particularly equal to 0.23.

In an alternative variant of this embodiment:
k is equal to 21.35;
a is equal to 0.62;
b is equal to 0.55;
c is equal to 0.14;
d is equal to −0.38; and
f is equal to −0.39;
and wherein the threshold value is comprised between 0.2319 and 0.6465, and is more particularly equal to 0.4343.

A third aspect of the invention relates to a method for calculating a NASH score which is indicative of non-alcoholic steatohepatitis (NASH), or of the activity, the stage, or the severity of NASH in a subject, wherein said score is based on the measure of at least one marker selected from either group (i), (ii) or (iii), and at least one marker selected from either group (iv) or (v) defined as follows:
  (i) alpha 2 macroglobulin
  (ii) glycated haemoglobin (HbA1c), fasting glucose level, fructosamine level
  (iii) N-terminal pro-peptide of collagen type III
  (iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
  (v) hsa-miR-200 (in particular hsa-miR-200a, more particularly hsa-miR-200a-3p).

In an embodiment of the third aspect, the following (i) to (v) measures are determined from a blood, serum or plasma sample of said subject:
  (i) the level of alpha 2 macroglobulin;
  (ii) the level of at least one marker selected in the group consisting of HbA1c, fasting glucose level, fructosamine level;
  (iii) the level of N-terminal pro-peptide of collagen type III;
  (iv) the level of at least one marker selected in the group consisting of hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p); and
  (v) the level of hsa-miR-200 (in particular hsa-miR-200a, more particularly hsa-miR-200a-3p).

In a particular embodiment of the third aspect, the method comprises determining the level of alpha 2 macroglobulin, HbA1c, N-terminal pro-peptide of collagen type III, hsa-miR-34 (in particular hsa-miR-34a, more particularly hsa-miR-34a-5p) and hsa-miR-200 (in particular hsa-miR-200a, more particularly hsa-miR-200a-3p), wherein the NASH score is calculated according to the following logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.

In a specific variant of this embodiment:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.

In another specific variant of this embodiment:
k is equal to 25.13;
a is equal to 0.6;
b is equal to 0.48;
c is equal to 0.1;
d is equal to −0.43; and
f is equal to −0.45.

In yet another specific variant of this embodiment:
k is equal to 21.35;
a is equal to 0.62;
b is equal to 0.55;
c is equal to 0.14;
d is equal to −0.38; and
f is equal to −0.39.

In a fourth aspect, the invention relates to a kit comprising means for determining the level of:
  (i) alpha 2 macroglobulin;
  (ii) at least one marker selected in the group consisting of HbA1c, fasting glucose level, fructosamine level;
  (iii) N-terminal pro-peptide of collagen type III;
  (iv) at least one marker selected in the group consisting of has-miR-34 (in particular hsa-miR-34a, more particularly hsa-miR-34a-5p), hsa-miR-122 (in particular hsa-miR-122-5p) and hsa-miR-192 (in particular hsa-miR-192-5p); and
  (v) hsa-miR-200 (in particular hsa-miR-200a, more particularly hsa-miR-200a-3p).

In an embodiment, the kit of the fourth aspect comprises means for determining the level of alpha 2 macroglobulin, HbA1c, N-terminal pro-peptide of collagen type III, hsa-miR-34 (in particular hsa-miR-34a, more particularly hsamiR-34a-5p) and hsa-miR-200 (in particular hsa-miR-200a, more particularly hsa-miR-200a-3p).

In a fifth aspect of the invention, the invention relates to a method for treating non-alcoholic steatohepatitis (NASH) in a subject, comprising:
(a) diagnosing NASH or determining the activity, the stage, or the severity of NASH in a subject according to the method described above;
(b) administering a treatment for NASH to said subject based on step (a).

In a sixth aspect, the invention relates to a method for treating non-alcoholic steatohepatitis (NASH) in a subject, comprising:
(a) classifying said subject according to the method described above;
(b) administering a treatment for NASH to the subject if said subject is classified as receiver of the treatment according to step (a).

In an embodiment of the fifth and sixth aspects, treatment comprises administering to the subject a compound of formula (I):

wherein:
X1 represents a halogen, a R1, or G1-R1 group;
A represents a CH=CH or a CH2-CH2 group;
X2 represents a G2-R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups;
or a pharmaceutically acceptable salt thereof.

In another particular embodiment of the fifth and sixth aspects, the compound is selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyloxyphenyl]prop-2-en-1-one, 2-[2,6-dimethyl-4-[3-[4-(methylthio)phenyl]-3-oxo-propyl] phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester; or a pharmaceutically acceptable salt thereof.

In another particular embodiment of the fifth and sixth aspects, the compound is 1-[4-methylthiophenyl]-3-[3,5-dimethyl-4-carboxydimethylmethyloxy phenyl]prop-2-en-1-one or a pharmaceutically acceptable salt thereof.

In another particular embodiment of the fifth and sixth aspects, the treatment comprises administering to the subject a compound of Table 1 as shown below.

Other aspects and embodiments will be apparent from the following detailed description.

DETAILED DESCRIPTION OF THE INVENTION

The invention relates to a method for the diagnosis of non-alcoholic steatohepatitis (NASH) or for determining the activity, the stage, or the severity of NASH in a subject. It also relates to a method for classifying a subject as a receiver or non receiver of a treatment for non-alcoholic steatohepatitis (NASH). This classification may also be the base for further determining whether a subject should undergo further confirmation of NASH by methods known in the art such as by undergoing liver biopsy.

The invention stems from the identification of a defined set of circulating markers that, when considered collectively, are indicative of NASH and/or of the activity, the stage, or the severity of NASH in the subject tested for NASH or for its severity or stage or activity. The invention relates in particular to a method for the diagnosis of non-alcoholic steatohepatitis (NASH) or for determining the activity, the stage, or the severity of NASH in a subject, combining the determination of the level of circulating micro-RNA(s) (miRNA(s)) and other circulating markers of liver damage.

Furthermore, the data collected by the inventors were processed according to two different biostatistical approaches leading to the determination of a score that is indicative of the disease and/or its severity or stage or activity, thereby providing a powerful, accurate and highly predictive tool for the physician to easily determine whether a subject is suffering from NASH, or to determine the stage or activity or severity of the disease. This score, otherwise termed "NASH score" in the following description, is an invaluable tool for both the practitioner and the subjects in need thereof, as it allows the diagnosis or the determination of the severity or stage or activity of NASH using a non-invasive procedure, i.e. without relying on liver biopsy.

The methods of the invention comprise the measure of at least one marker which is a micro-RNA marker and at least one other circulating markers of liver damage. The methods of the invention more particularly comprise the measure of the level of at least one marker selected from groups (i), (ii), and (iii), and at least one marker selected from groups (iv) and (v) below.

In a particular embodiment, the methods of the invention comprise the measure of the level of:

at least one marker selected in groups (i), (ii) and (iii) and at least one marker from each groups (iv) and (v);

at least one marker selected from each groups (i) and (ii) or (ii) and (iii) or (i) and (iii), and at least one marker selected from groups (iv) and (v);

at least one marker selected from each groups (i), (ii) and (iii) and at least one marker selected from groups (iv) and (v);

at least one marker in each groups of markers (i), (ii), (iii), (iv) and (v) below, i.e.:
the marker listed in (i); and
at least one marker listed in (ii); and
the marker listed in (iii); and
at least one marker listed in (iv);
the marker listed in (v).

The groups of markers are defined as follows:
(i) alpha 2 macroglobulin
(ii) glycated haemoglobin (HbA1c), fasting glucose level, fructosamine level
(iii) N-terminal pro-peptide of collagen type III
(iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
(v) hsa-miR-200 (in particular hsa-miR-200a, more particularly hsa-miR-200a-3p).

According to the present invention "non-alcoholic steatohepatitis" or "NASH" is defined as the presence of liver steatosis, hepatocyte ballooning and liver inflammation. To this basic definition of the disease, NASH may further include liver fibrosis.

According to the present invention, the subject is a mammal, in particular a human subject. The invention, thanks to its non-invasive nature, may be implemented on any subject, such as a subject with no known or suspected predisposition to NASH. However, in a particular embodiment, the subject is a subject at risk of having NASH or of developing NASH in the future, such as a subject having obesity, diabetes, suffering from the metabolic syndrome, or having elevated liver enzymes, or who was previously diagnosed with non-alcoholic fatty liver disease (or liver steatosis). The subject may also be a subject with already identified NASH, the method of the invention thereby allowing determining the risks of evolution of the disease towards hepatocarcinoma or liver transplantation or a cardiovascular disease.

The levels of the markers measured in the present invention are determined from a body fluid of the subject, which may in particular be a blood, more particularly serum or plasma sample.

The level of the markers identified by the inventors may be determined by conventional methods well known in the art, such as immunoassays (e.g. ELISA), or molecular and biochemical assays (quantitative PCR, colorimetric assays), or analytical methods (such as mass spectrometry), depending on the biomarker type (such as a protein, a micro-RNA, glucose level, . . . ). When the tested marker is a micro-RNA, its measure may be carried out according to a number of methods well-known in the art, such as that presented in the examples below. Briefly, the measures are carried out from total RNA extracted from a plasma sample, in particular a cell-free, platelet-free plasma sample. An appropriate internal control (such as a micro-RNA of known sequence and quantity, e.g. *C. elegans* miR-39) may be added to the sample before RNA extraction. Cq values are determined using quantitative PCR. Commercial kits are available for conducting such assays. For example, the Taqman miRNA qRT-PCR assay: Taqman MicroRNA Reverse transcription Kit, TaqMan MicroRNA Assay 20×, and TaqMan Universal Master Mix II (Applied Biosystems) may be used according to the manufacturer's instructions. Reverse transcription may be performed using readily available PCR systems, such as the GeneAmp® PCR System 9700 thermal cycler (Applied Biosystems), with appropriate cycling parameters such as 16° C. for 30 minutes followed by 42° C. for 30 minutes and 85° C. for 5 minutes before holding at 4° C. The reverse transcription may be implemented in the multiplexed format. Quantitative PCT is then conducted using a quantitative PCR system such as the CFX96™ Real-Time System (C1000 Touch™ Thermal Cycler, BioRad). Cycling conditions may be the following: 95° C. for 10 minutes followed by 95° C. for 15 sec and 60° C. for 60 sec for a total of 50 cycles and 30° C. for 30 sec. Cq determination mode may be set of Regression in the quantitative PCR system. In a particular embodiment, the Cq value determined according to the method of the invention is the Cq value which is obtainable using the above specific parameters and material. Cq values of samples may be excluded from the analysis if values are above the maximum Cq of the standard curve of each miRNA. The standard curve may be used to assess the reaction efficiency. Serial dilution may be performed over eight points starting from the most concentrated cDNA sample, to ensure the standard curve covers all potential template concentrations that may be encountered during the study. The standard curve may be constructed by plotting the log of the starting quantity of the template against the Cq values obtained.

According to the present invention, a subject is diagnosed having NASH, or is diagnosed as potentially having NASH or likely to have NASH, when all the levels of markers selected and measured in each of group (i) to (v) are increased when compared to reference values obtained from a control (or reference) sample. The reference sample may correspond to a body fluid sample, such as a blood, serum or plasma sample obtained from one or more subjects, such as two or more, who do not have NAFLD or NASH.

In the present invention, the levels of biomarkers measured as described above may also be used to determine a disease score, otherwise named NASH score. The disease score may be compared with a threshold value that distinguishes between low, moderate, and high NASH activity, or moderate and severe NASH. According to the present invention, this information may be advantageously used to determine whether a subject will receive or not a therapeutic treatment for NASH. Only those subjects with a moderate to high NASH activity or severe NASH will be treated. Accordingly, the present invention relates to a method for classifying a subject as a receiver or non receiver of a treatment for non-alcoholic steatohepatitis (NASH), said method comprising the determination of the levels of the markers as defined above, the calculation of a NASH score, and the classification of the subject as receiver or non receiver of the treatment based on said NASH score. In addition, the classification of the subject may also be used to determine a low NASH activity or a moderate NASH in the subject, and providing to the subject based on this classification diet and lifestyle recommendations to reverse NASH.

According to the present invention, those subjects classified as moderate to high NASH activity, or as severe NASH patients are considered as receivers, or potential receivers, of a treatment for NASH. In the context of the present invention, a moderate to high NASH activity or a severe NASH patient is defined as, or equivalent to, a patient presenting the following liver biopsy-derived grades:

steatosis grade ≥1
hepatocyte ballooning grade ≥1
lobular inflammation grade ≥1
NAS (NAFLD Activity Score) ≥4 (NAS is defined as the sum of the steatosis grade, hepatocyte ballooning grade and lobular inflammation grade)
fibrosis stage ≥2 (such as a fibrosis equal to 2, 3 or 4, in particular 2 or 3)

In a particular embodiment, the NASH score of the invention is calculated from the following marker levels measured as provided above:
level of alpha 2 macroglobulin (LVBP_A2M_GL); and
level of HbA1c (LBBC_HBA1C_PERC); and
level of N-terminal pro-peptide of collagen type III (LVB_P3NP); and
level of hsa-miR-34 (in particular miR-34a, more particularly miR-34a-5p) (LVMK_HSA_MIR34A_MULTI1_CQ); and
level of hsa-miR-200 (in particular hsa-miR-200a, more particularly hsa-miR-200a-3p) (LVMK_HSA_MIR200A_MULTI1_CQ).

In a further particular embodiment, the score is defined as a logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent (e.g. B is equal to 10 if measured HbA1c percentage is 10%);
C is the level of N-terminal pro-peptide of collagen type III in ng/mL;
D is the level of hsa-miR-34 (in particular hsa-miR-34a, more particularly hsa-miR-34a-5p) in Cq;
F is the level of hsa-miR-200 (in particular c hsa-miR-200a, more particularly hsa-miR-200a-3p) in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.

In a further particular embodiment, the score is calculated according to the above logistic function, wherein:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.

The NASH score thus is the probability of having a moderate to high NASH activity or a severe NASH. If S as determined for a subject is greater or equal to a threshold value, the subject is classified as to be treated for NASH, or to potentially be treated for NASH. If S is lower than a threshold value, the subject is classified as not to be treated, and/or the subject is classified as receiver, or potential receiver, of diet and lifestyle advices for managing its low NASH activity or moderate NASH.

According to a particular embodiment, the subject is classified as a receiver, or potential receiver, of a treatment if S is higher than or equal to a threshold value comprised between 0.102 and 0.6465.

In a particular embodiment, derived from the median model as described in the experimental part of this application:
k is equal to 25.13;
a is equal to 0.6;
b is equal to 0.48;
c is equal to 0.1;
d is equal to −0.43; and
f is equal to −0.45;
and wherein the threshold value is comprised between 0.102 and 0.462, and is more particularly equal to 0.23.

In a particular embodiment, derived from the bootstrap model as described in the experimental part of this application:
k is equal to 21.35;
a is equal to 0.62;
b is equal to 0.55;
c is equal to 0.14;
d is equal to −0.38; and
f is equal to −0.39;
and wherein the threshold value is comprised between 0.2319 and 0.6465, and is more particularly equal to 0.4343.

The present invention also relates to a kit comprising means for determining the level of:
(i) alpha 2 macroglobulin;
(ii) at least one marker selected in the group consisting of HbA1c, fasting glucose level, fructosamine level;
(iii) N-terminal pro-peptide of collagen type III;
(iv) at least one marker selected in the group consisting of hsa-miR-34 (in particular hsa-miR-34a, more particularly miR-34a-5p), hsa-miR-122 (in particular hsa-miR-122-5p) and hsa-miR-192 (in particular hsa-miR-192-5p); and
(v) hsa-miR-200 (in particular hsa-miR-200a, more particularly hsa-miR-200a-3p).

In a particular embodiment of the invention, said kit comprises means for determining the level of alpha 2 macroglobulin, HbA1c, N-terminal pro-peptide of collagen type III, hsa-miR-34 (in particular hsa-miR-34a, more particularly miR-34a-5p) and hsa-miR-200a (in particular hsa-miR-200a, more particularly hsa-miR-200a-3p).

The kit of the invention is useful for implementing the methods described above may further optionally include instructions for implementing said methods. The kit may comprise reagents and buffers appropriate for conducting measures of the levels of markers identified above. In particular, the kit may comprise antibodies specific for a protein to be quantified, and/or primers useful for quantifying micro-RNA levels, as well-known in the art.

The present invention further relates to a method for treating NASH in a subject, comprising:
(a) diagnosing NASH or determining the activity, the stage, or the severity of NASH in a subject according to the methods provided above;
(b) administering a treatment for NASH to said subject based on step (a).

The present invention further relates to a method for treating NASH in a subject, comprising:
(a) classifying said subject according to the method of classification as defined above;
(b) administering a treatment for NASH to the subject if said subject is classified as receiver of the treatment according to step (a).

The present invention further relates to a method for managing low NASH activity, or moderate NASH in a subject, comprising:
(a) classifying said subject according to the method of classification as defined above;
(b) providing diet and lifestyle recommendations to the subject if said subject is classified as non receiver of the treatment according to step (a).

The method for treating NASH according to the present invention comprise the administration of one or more compound(s) to the subject in need thereof such as a compound of formula (I):

wherein:
X1 represents a halogen, a R1, or G1-R1 group;
A represents a CH=CH or a CH2-CH2 group;
X2 represents a G2-R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups;
or a pharmaceutically acceptable salt thereof.

In a particular embodiment of this method for the treatment of NASH, the compound of formula (I) is selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyloxyphenyl]prop-2-en-1-one, 2-[2,6-dimethyl-4-[3-[4-(methylthio)phenyl]-3-oxo-propyl]phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester; or a pharmaceutically acceptable salt thereof. In a further particular embodiment of the invention, the compound of formula (I) is 1-[4-methylthiophenyl]-3-[3,5-dimethyl-4-carboxydimethylmethyloxy phenyl]prop-2-en-1-one or a pharmaceutically acceptable salt thereof.

Other compounds that might be used in the method for the treatment of NASH of the present invention may include, without limitation, a compound selected from the following classes and specific compounds of table 1.

TABLE 1

| Class | Compound |
|---|---|
| Alanine transaminase stimulator | HU-002 |
| 11-beta hydroxysteroid dehydrogenase (HSD) inhibitor | RO5093151 |
| Aldosterone antagonist, anti-oxydant | Spirono-lactone/Vit E |
| Amino-acid | SAMe (S-adenosyl-L-methionine) |
| Analog of human leptin | Metreleptin |
| Anti-apoptotic caspase inhibitor | Emricasan (IDN-6556) |
| Antibiotic | Rifaximin |
| Anti-oxidant | MitoQ |
|  | Vitamin E |
| Anti-Oxidant PPARγ | Vitamin E Pioglitazone |
| Anti-oxydant | Cysteamine (Cystagon-EC) |
|  | Siliphos |
| Anti-oxydant Biguanide | Vitamin E Metformin |
| Bovine Colostrum Inflammation | IMM 124-E |
| Caspase Inib | GS-9450 |
| SCD1 inhibitors | Aramchol |
| DGAT1 inhibitors | LCQ908 |
| Fish oil supplement | Omega 3 |
|  | PUFA Opti-EPA |
| Flavonoid | MEDOX (Anthocyanin) |
|  | Silymarin |
| FXR agonist | OCA (obeticholic acid) |
| galectin inhibitor | GR-MD-02 |
| GLP-1 Agonist | Exenatide |
| GLP1 mimetic | Liraglutide |
| Immune-modulator | Oral anti a-CD3 |
|  | EGS21 |
| Bile acids | UDCA |
| Iron Chelator | Deferasirox ICL 670 Exjade ® |
| Lipid Lowering agent | Ezetimibe |
| musculotropic vasodilator | Pentoxifylline |
| Omega 3 | Lovaza |
|  | EPA-E (MND-21) |

EXAMPLES

Sample Collection and Analysis
Clinical Study

The clinical trial (phase 2 GOLDEN-505 trial in NASH (GFT505-212-7-NCT01694849) is a multicentre, randomized, double blind, placebo-controlled study to evaluate the efficacy and safety of Elafibranor (1-[4-methylthiophenyl]-3-[3,5-dimethyl-4-carboxydimethylmethyloxy phenyl]prop-2-en-1-one) once daily on steatohepatitis in patients with non-alcoholic steatohepatitis (NASH). Liver biopsy was performed to confirm the diagnosis of NASH after appropriate exclusion of liver disease of other etiology. NASH was diagnosed as steatohepatitis evaluated by liver biopsy within 6 months before randomization. Steatohepatitis confirmation was based on central reading of liver biopsies. NASH patients were defined with a NAS ≥3 including steatosis grade ≥1 and hepatocyte ballooning ≥1 and lobular inflammation ≥1.

The study was approved by appropriate regulatory bodies at each participating center and all patients had given consent for participation in medical research.
Blood Sampling and Laboratory Testing Blood samples were collected according to the Central Laboratory Protocol and Manual-Genfit-GFT505-212-7.

According to the study protocol, following analyses were performed.

HEMATOLOGY includes hemoglobin, hematocrit, RBC count, leukocytes, differential leukocyte count (neutrophils, lymphocytes, eosinophils, monocytes, basophils-abs. and % values), platelets and reticulocytes.

BIOCHEMISTRY Panel I includes plasma glucose, triglycerides (TG), creatinine, creatinine clearance, gamma-glutamyltransferase (GGT), aspartate aminotransferase (AST), alanine aminotransferase (ALT), creatine phosphokinase (CPK), alkaline phosphatase, thyroid stimulating hormone (TSH) and HbA1c.

BIOCHEMISTRY Panel II includes plasma glucose, creatinine, creatinine clearance, total protein, albumin, sodium, potassium, chloride, calcium, uric acid, urea expressed as blood urea nitrogen (BUN), aspartate aminotransferase (AST), alanine aminotransferase (ALT), gamma-glutamyltransferase (GGT), alkaline phosphatase, creatine phosphokinase (CPK), bilirubin total, bilirubin conjugated, C-reactive protein (hsCRP), AST/ALT Ratio and HbA1c.

URINALYSIS includes:
Dipstick analysis (specific gravity, pH, RBC, leukocytes, glucose, protein, ketones, bilirubin, urobilinogen and nitrite)
Microscopy analysis includes RBC, WBC, casts, crystals, bacteria, epithelial cells and yeasts.
Chemistry analysis (albumin and creatinine)

SEROLOGY includes HIV ab I/II, HCV ab, HCV RNA (only tested upon receipt of HCV RNA Visit samples and in case of 'reactive' or 'indeterminate' result for HCV Ab) and HbsAg.

LIPID PANEL includes triglycerides (TG), total cholesterol, non HDL-C (calculation), high-density lipoprotein cholesterol (HDL-C), low density lipoprotein (LDL-C) (calculation), calculated very low density lipoprotein cholesterol (VLDL-C) (calculation), apolipoprotein AI (ApoAI) and apolipoprotein B (ApoB).

URINE CHEMISTRY includes alpha-1-microglobulin, beta-N-acetylglucosaminidase (beta-NAG) and neutrophil-gelatinase associated lipocalin (N-Gal)

SAFETY MARKERS includes homocysteine, NT-ProBNP, Troponin T, Cystatin C, and Beta2-microglobulin.

GLYCEMIC AND OTHER LIPIDIC PARAMETERS includes leptin, insulin, homeostatic model assement (HOMA-IR), serum glucose (for calculation of HOMA-IR), fructosamine, C-peptide and free fatty acids (FFA).

INFLAMMATORY MARKERS includes haptoglobin, fibrinogen, tumor necrosis factor alpha (TNF-α), interleukin 6 (IL-6) and plasminogen activator inhibitor 1 (PAI-1) Ag (citrate).

LIVER MARKERS includes cytokeratin-18 (CK18) (M65 & M30), adinopectin, ferritin, alpha2 macroglobulin, FGF19 & FGF21, hyaluronic acid (Advia centaur, reagentiaprocured by Siemens Belgium and charged to Genfit in pass-through), N-terminal pro-peptide of collagen type III (PIIINP) (Advia centaur, reagentia procured by Siemens Belgium) and tissue inhibitor of matrix metalloprotease-1 (TIMP-1) (Advia centaur, reagentiaprocured by Siemens).

Sample Collection & Storage

Blood samples used in this biomarker study were drawn from patients of the 505.212.7 study before treatment period. Written, informed consent for collection, storage and use of additional samples was obtained from every patient.

Blood collected in citrate containing tubes 2.7 mL was processed by separating cell-free plasma from blood cells within 15 minutes of collection by centrifugation at 1,500×g for 15 minutes. The supernatant plasma was transferred to a new tube. Tubes were kept at −70° C.

To proceed to RNA extraction, plasma tubes were then centrifuged at 13,000×g for 2 min to pellet and remove the platelets. The supernatant platelet-free plasma was transferred to a new tube, frozen in liquid nitrogen and stored at −80° C.

Total RNA Extraction and Quantitation of miRNA

Total RNA with preserved miRNAs was extracted from 400 µl of platelet-free plasma by miRNeasy extraction kit (miRNeasy Serum/Plasma Kit (cat. no. 217184)) and using a plasma/QIAzol ratio of 1:5 according to the manufacturer's instructions. Synthetic spiked-in C. elegans miR-39 was added to the samples [3,125 fmoles] prior to RNA extraction as internal control of RNA extraction process. The elution was performed in 18 µl of elution buffer.

Expression of mature miRNAs was detected according to the manufacturer's instructions using the Taqman miRNA qRT-PCR Assay: TaqMan MicroRNA Reverse transcription Kit (Ref: 4366596, Applied Biosystems, Carlsbad, Calif.), TaqMan MicroRNA Assay 20× (Ref: 4440887, Applied Biosystems) and TaqMan Universal Master Mix II (Ref: 4440040, Applied Biosystems).

Reverse Transcription were performed using a GeneAmp® PCR System 9700 thermal cycler (Ref: 200005, Applied Biosystems) with cycling conditions of 16° C. for 30 minutes followed by 42° C. for 30 minutes and 85° C. for 5 minutes before holding at 4° C. The Reverse transcription was multiplexed with 4 miRNA specific-reverse primers in order to conserve RNA sample.

Quantitative PCR were performed using a CFX96™ Real-Time System (C1000 Touch™ Thermal Cycler, Bio-Rad) with cycling conditions of 95° C. for 10 minutes followed by 95° C. for 15 sec and 60° C. for 60 sec for a total of 50 cycles and 30° C. for 30 sec.

The sequences of specific primers for miRNA of potential interest were chosen according to the following table 2.

TABLE 2 sequences of tested miRNA

| Mature miRNA | Assay id (Life Technologies) | Sequence of mature miRNA | mirBase number | Supplier |
|---|---|---|---|---|
| cel-miR-39-3p | 000200 | UCACCGGGUGUAAAUCAGCUUG (SEQ ID NO: 1) | MIMAT0000010 | Life technologies |
| hsa-miR-122-5p | 002245 | UGGAGUGUGACAAUGGUGUUUG (SEQ ID NO: 2) | MIMAT0000421 | Life technologies |
| hsa-miR-34a-5p | 000426 | UGGCAGUGUCUUAGCUGGUUGU (SEQ ID NO: 3) | MIMAT0000255 | Life technologies |

TABLE 2-continued sequences of tested miRNA

| Mature miRNA | Assay id (Life Technologies) | Sequence of mature miRNA | mirBase number | Supplier |
|---|---|---|---|---|
| hsa-miR-200a-3p | 000502 | UAACACUGUCUGGUAACGAUGU (SEQ ID NO: 4) | MIMAT0000318 | Life technologies |
| hsa-miR-29b-3p | 000413 | UAGCACCAUUUGAAAUCAGUGUU (SEQ ID NO: 5) | MIMAT0000100 | Life technologies |
| hsa-miR-192-5p | 000491 | CUGACCUAUGAAUUGACAGCC (SEQ ID NO: 6) | MIMAT0000222 | Life technologies |
| hsa-miR-221-3p | 000524 | AGCUACAUUGUCUGCUGGGUUUC (SEQ ID NO: 7) | MIMAT0000278 | Life technologies |
| hsa-miR-103a-3p | 000439 | AGCAGCAUUGUACAGGGCUAUGA (SEQ ID NO: 8) | MIMAT0000101 | Life technologies |
| hsa-miR-155-5p | 002623 | UUAAUGCUAAUCGUGAUAGGGGU (SEQ ID NO: 9) | MIMAT0000646 | Life technologies |
| hsa-miR-199a-5p | 000498 | CCCAGUGUUCAGACUACCUGUUC (SEQ ID NO: 10) | MIMAT0000231 | Life technologies |

Data used in the construction of the algorithm were in Cq format. The Cq Determination mode was Regression.

Statistical Analysis

Objective and Definition

The objective of these analyses was to discover biomarkers that can be related to the identification of NASH patients to be treated. Patients to be treated (TBT) were defined as:

Fibrosis stage ≥2 and

NAS ≥4 and

Lobular inflammation grade ≥1 and

Steatosis grade ≥1 and

Ballooning grade ≥1.

Other patients were stated as not to be treated (NTBT). For the analysis, TBT patients were categorized as 1 and NTBT as 0 in the response variable. As shown above, explicative variables encompassed a wide range of biomarkers measured in blood (hematology, biochemistry, coagulation, liver markers, circulating miRNA) or in urinary (dipstick, sediment) samples, as long as demographic (age, sex, race), region (study centre, country, continent) or medical (diabetes) recordings.

Dataset Management

The dataset used in this study was coming from the Golden-505 trial and was initially composed of 274 patients and 121 variables. The dataset management included the following steps:
1. Removal of 28 patients without miRNAs measurement
2. Removal of 9 variables with more than 10 missing values
3. Removal of 7 patients with extreme values and 28 with remaining missing values It resulted in a dataset with 211 patients and 112 variables that were used to test collinearity between explicative variables.

Test of Collinearity

Pearson correlation was calculated two by two between quantitative variables. When two variables presented a correlation superior to 0.7, univariate test of difference in their mean in relation to the response variable defining patients TBT were done. The selected variable was the more significant. The collinear and selected variables are presented in Table 2.

Thirty-five unique collinear variables where removed and the final dataset used in the analysis included 77 variables (patient id, response variable, 5 histological grades and 70 explicative variables) and 211 patients (95 TBT and 116 NTBT).

TABLE 3

Selected and dropped variables in collinearity test

| Selected variables in collinear variables | Dropped variables in collinear variables | |
|---|---|---|
| GLP_HOMA_IR | GLP_INS_PMOLL | GLP_CPEPTID_NMOLL |
| INMK_CK18_M65_UL | LVBP_CK18_M30_PMOLL | LBBC_AST_UIL |
| INMK_FGF_21_PGML | SFMK_HOMOCYS_UMOLL | |
| LBBC_HBA1C_PERC | LBBC_GLU_FAST_MMOLL | GLP_GLU_FAST_MMOLL |
| LBHA_BASO_10_9_L | LBHA_BASO_PERC | |
| LBHA_EOSINO_10_9_L | LBHA_EOSINO_PERC | |
| LBHA_HEMATO_VV | LBHA_HEMO_GL | LBHA_RBC_COUNT_10_12_L |
| LBHA_LEUKO_10_9_L | LBHA_NEUTRO_10_9_L | |
| LBHA_LYMPHO_PERC | LBHA_NEUTRO_PERC | |
| LBHA_PROTHR_TIME_SEC | LBHA_INR | LBHA_PROTHR_TIME_PERC |
| LBHA_RETICULO_10_9_L | LBHA_RETICULO_RBC | |
| LBLP_LIPOPRINT_HDL_MGDL | LBLP_HDL_MMOLL | LBLP_APOA1_MGDL |

TABLE 3-continued

Selected and dropped variables in collinearity test

| | | |
|---|---|---|
| LBLP_LIPOPRINT_IDLA_MGDL | LBLP_LIPOPRINT_LDL1_MGDL | |
| LBLP_LIPOPRINT_IDLB_MGDL | LBLP_NHDL_MMOLL | |
| LBLP_LIPOPRINT_IDLC_MGDL | LBLP_TC_MMOLL | LBLP_LDL_MMOLL |
| LBLP_LIPOPRINT_LDL2_MGDL | LBLP_APOB_MGDL | LBLP_NHDL_MMOLL |
| LBLP_TG_MMOLL | LBLP_VLDL_MMOLL | LBLP_LIPOPRINT_VLDL_MGDL |
| LVMK_HSA_MIR103_MULTI1_CQ | LVMK_HSA_MIR155_MULTI1_CQ | LVMK_HSA_MIR199A_MULTI1_CQ |
| LVMK_HSA_MIR34A_MULTI1_CQ | LVMK_HSA_MIR122_MULTI1_CQ | LVMK_HSA_MIR192_MULTI1_CQ |
| URI_SPECGRAV | URI_CREAT_GL | |
| WAIST | BMI | WEIGHT |

| Selected variables in collinear variables | Dropped variables in collinear variables | |
|---|---|---|
| GLP_HOMA_IR | | |
| INMK_CK18_M65_UL | LBBC_ALT_UIL | |
| INMK_FGF_21_PGML | | |
| LBBC_HBA1C_PERC | GLP_FRUCTO_UMOLL | |
| LBHA_BASO_10_9_L | | |
| LBHA_EOSINO_10_9_L | | |
| LBHA_HEMATO_VV | | |
| LBHA_LEUKO_10_9_L | | |
| LBHA_LYMPHO_PERC | | |
| LBHA_PROTHR_TIME_SEC | | |
| LBHA_RETICULO_10_9_L | | |
| LBLP_LIPOPRINT_HDL_MGDL | | |
| LBLP_LIPOPRINT_IDLA_MGDL | | |
| LBLP_LIPOPRINT_IDLB_MGDL | | |
| LBLP_LIPOPRINT_IDLC_MGDL | LBLP_APOB_MGDL | LBLP_NHDL_MMOLL |
| LBLP_LIPOPRINT_LDL2_MGDL | | |
| LBLP_TG_MMOLL | | |
| LVMK_HSA_MIR103_MULTI1_CQ | LVMK_HSA_MIR221_MULTI1_CQ | |
| LVMK_HSA_MIR34A_MULTI1_CQ | | |
| URI_SPECGRAV | | |
| WAIST | | |

| Variables | Parameter |
|---|---|
| GLP_HOMA_IR | Homeostatic Model Assesment (HOMA-IR) |
| INMK_CK18_M65_UL | Cytokeratin-18 (CK18) (M65) |
| INMK_FGF_21_PGML | FGF21 |
| LBBC_HBA1C_PERC | HbA1c |
| LBHA_BASO_10_9_L | Basophils (abs.) |
| LBHA_EOSINO_10_9_L | Eosinophils (abs) |
| LBHA_HEMATO_VV | Hematocrit |
| LBHA_LEUKO_10_9_L | Leukocytes |
| LBHA_LYMPHO_PERC | Lymphocytes (%) |
| LBHA_PROTHR_TIME_SEC | Prothrombin time (sec) |
| LBHA_RETICULO_10_9_L | Reticulocytes (abs.) |
| LBLP_LIPOPRINT_HDL_MGDL | High-density lipoprotein (HDL) |
| LBLP_LIPOPRINT_IDLA_MGDL | Intermediate-density lipoprotein |
| LBLP_LIPOPRINT_IDLB_MGDL | Intermediate-density lipoprotein |
| LBLP_LIPOPRINT_IDLC_MGDL | Intermediate-density lipoprotein |
| LBLP_LIPOPRINT_LDL2_MGDL | low Density Lipoprotein (LDL) |
| LBLP_TG_MMOLL | Triglycerides |
| lvmk_hsa_mir103_multi1_cq | miRNA103 |
| lvmk_hsa_mir34a_multi1_cq | miRNA34a |
| URI_SPECGRAV | Specific gravity |
| GLP_INS_PMOLL | insulin |
| LVBP_CK18_M30_PMOLL | cytokeratin-18 (CK18) (M30) |
| SFMK_HOMOCYS_UMOLL | homocysteine |
| LBBC_GLU_FAST_MMOLL | glucose |
| LBHA_BASO_PERC | basophils (%) |
| LBHA_EOSINO_PERC | eosinophils (%) |
| LBHA_HEMO_GL | hemoglobin |
| LBHA_NEUTRO_10_9_L | neutrophils (abs) |
| LBHA_NEUTRO_PERC | neutrophils (%) |
| LBHA_INR | INR |
| LBHA_RETICULO_RBC | reticulocytes (% of RBC) |
| LBLP_HDL_MMOLL | high-density lipoprotein cholesterol (HDL-C) |
| LBLP_LIPOPRINT_LDL1_MGDL | low Density Lipoprotein (LDL) |
| LBLP_NHDL_MMOLL | non HDL-C |
| LBLP_TC_MMOLL | total cholesterol |
| LBLP_APOB_MGDL | apolipoprotein B (Apo B) |
| LBLP_VLDL_MMOLL | calculated Very Low Density Lipoprotein Cholesterol (VLDL-C) |
| lvmk_hsa_mir155_multi1_cq | miR155 |
| lvmk_hsa_mir122_multi1_cq | miR122 |
| URI_CREAT_GL | creatinine |
| bmi | body mass index |

TABLE 3-continued

Selected and dropped variables in collinearity test

| | |
|---|---|
| GLP_CPEPTID_NMOLL | C-peptide |
| LBBC_AST_UIL | Aspartate Aminotransferase (AST) |
| GLP_GLU_FAST_MMOLL | glucose |
| LBHA_RBC_COUNT_10_12_L | RBC Count |
| LBHA_PROTHR_TIME_PERC | Prothrombin time |
| LBLP_APOA1_MGDL | Apolipoprotein AI (Apo AI) |
| LBLP_LDL_MMOLL | Low Density Lipoprotein (LDL-C) |
| LBLP_LIPOPRINT_VLDL_MGDL | Very Low Density Lipoprotein Cholesterol |
| lvmk_hsa_mir199a_multi1_cq | miR199a |
| lvmk_hsa-mir192_multi1_cq | miR192 |
| LBBC_ALT_UIL | Alanine Aminotransferase (ALT) |
| GLP_FRUCTO_UMOLL | Fructosamine |
| lvmk_hsa_mir221_multi1_cq | miR221 |

Median Model

Dataset was partitioned one million times in ⅔ training set and in ⅓ verification set, stratified on TBT and NTBT patient distribution. In these different possible partitions, 27,477 presented no significant difference between the training and verification sets in all explicative variables and histological grades and were used for analysis.

A logistic regression was performed between the response variable and 70 explicative variables, followed by a variable selection using the Akaike Information Criterion (AIC), in the 27,477 training sets. It resulted in 27,477 different coefficients for the 70 variables. The median model was created by combining variables with a median coefficient different from zero (Table 4).

TABLE 4

Results of median model ($^{cor}$: collinear variable)

| Variables included in median model | Coefficients | $1^{st}$-$3^{rd}$ quartiles |
|---|---|---|
| Constant | 25.13 | 18.39; 32.66 |
| LVBP_A2M_GL | 0.60 | 0.43; 0.77 |
| LBBC_HBA1C_PERC $^{cor}$ | 0.48 | 0.001; 0.69 |
| LVB_P3NP | 0.10 | 0.001; 0.14 |
| lvmk_hsa_mir34a_multi1_cq $^{cor}$ | −0.43 | −0.60; −0.001 |
| lvmk_hsa_mir200a_multi1_cq | −0.45 | −0.58; −0.31 |

LVBP_A2M_GL: Alpha 2 macroglobuline; LBBC_HBA1C_PERC: HbA1c; LVB_P3NP: N-terminal pro-peptide of collagen type III; lvmk_hsa_mir34a_multi1_cq: miR-34a; lvmk_hsa_mir200a_multi1_cq: miR-200a.

The model was then verified by calculating the Area Under the ROC curve (AUC) for each of the 27.477 sets. The AUC was of 0.82 (95% CI: 0.72-0.91). Using the median AUC, 3 thresholds were defined for predicting patients as TBT or NTBT:

1. The threshold closest to the point with 1-Specificity=0% and Sensitivity=100% equalled 0.23. The corresponding contingency table is presented in Table 5a and produced the following indices:
   Total accuracy: 80.28%
   Sensitivity: 81.25%
   Specificity: 79.49%
   PPV (Positive Predictive Value): 76.47%
   NPV (Negative Predictive Value): 83.78%
2. The threshold giving a sensitivity superior to 90% equalled 0.102. The corresponding contingency table is presented in Table 5b and produced the following indices:
   Total accuracy: 63.38%
   Sensitivity: 90.63%
   Specificity: 41.03%
   PPV (Positive Predictive Value): 55.77%
   NPV (Negative Predictive Value): 84.21%
3. The threshold giving a specificity superior to 90% equalled 0.462. The corresponding contingency table is presented in Table 5c and produced the following indices:
   Total accuracy: 70.42%
   Sensitivity: 43.75%
   Specificity: 92.31%
   PPV (Positive Predictive Value): 82.35%
   NPV (Negative Predictive Value): 66.67%

TABLE 5a

Contingency table of TBT/NTBT patients observed and predicted by the median model and a threshold of 0.23.

| | Predicted | NTBT (0) | TBT (1) |
|---|---|---|---|
| Observed | NTBT (0) | 31 | 8 |
| | TBT (1) | 6 | 26 |

TABLE 5b

Contingency table of TBT/NTBT patients observed and predicted by the median model and a threshold of 0.102.

| | Predicted | NTBT (0) | TBT (1) |
|---|---|---|---|
| Observed | NTBT (0) | 16 | 23 |
| | TBT (1) | 3 | 29 |

TABLE 5c

Contingency table of TBT/NTBT patients observed and predicted by the median model and a threshold of 0.462.

| | Predicted | NTBT (0) | TBT (1) |
|---|---|---|---|
| Observed | NTBT (0) | 36 | 3 |
| | TBT (1) | 18 | 14 |

Bootstrap Model

Using all 211 patients a logistic regression was calculated as full model using all 70 explicative variables and an optimal model is obtained by selecting variables with the AIC (Table 6). The significance of variable coefficients was then tested using 1000 bootstrap samples (Table 6).

TABLE 6

Results of bootstrap model ($^{cor}$: collinear variable)

| Variables included in median model | Coefficients | 95% CI |
|---|---|---|
| Constant | 21.35 | 5.26; 36.76 |
| LVBP_A2M_GL | 0.62 | 0.11; 1.07 |
| LBBC_HBA1C_PERC $^{cor}$ | 0.55 | 0.13; 1.02 |
| LVB_P3NP | 0.14 | 0.03; 0.23 |
| lvmk_hsa_mir34a_multi1_cq $^{cor}$ | −0.38 | −0.77; −0.001 |
| lvmk_hsa_mir200a_multi1_cq | −0.39 | −0.78; −0.04 |

Of outmost importance, it is very satisfying to note that the variables identified with the bootstrap model are the same as those identified with the median model described above. This observation strengthens the statistical relevance and confidence of these variables as predictive of NASH and of its stage or severity.

The optimal model is verified by calculating the AUC in 1000 bootstrap samples. The AUC was of 0.82 (95% CI: 0.76-0.87). Using the AUC of the optimal model, 3 thresholds were defined for predicting patients as TBT or NTBT:

1. The threshold closest to the point with 1-Specificity=0% and Sensitivity=100%, equalled 0.4343. The corresponding contingency table is presented in Table 7a and produced the following indices:
   Total accuracy: 75.36%
   Sensitivity: 74.74%
   Specificity: 75.86%
   PPV: 71.72%
   NPV (Negative Predictive Value): 78.57%
2. The threshold giving a sensitivity superior to 90% equalled 0.2319. The corresponding contingency table is presented in Table 7b and produced the following indices:
   Total accuracy: 65.88%
   Sensitivity: 90.53%
   Specificity: 45.69%
   PPV (Positive Predictive Value): 57.72%
   NPV (Negative Predictive Value): 85.48%
3. The threshold giving a specificity superior to 90% equalled 0.6465. The corresponding contingency table is presented in Table 7c and produced the following indices:
   Total accuracy: 73.46%
   Sensitivity: 52.63%
   Specificity: 90.52%
   PPV (Positive Predictive Value): 81.97%
   NPV (Negative Predictive Value): 70.00%

TABLE 7a

Contingency table of TBT/NTBT patients observed and predicted by the bootstrap model and a threshold of 0.4343.

| | Predicted | NTBT (0) | TBT (1) |
|---|---|---|---|
| Observed | NTBT (0) | 88 | 28 |
| | TBT (1) | 24 | 71 |

TABLE 7b

Contingency table of TBT/NTBT patients observed and predicted by the bootstrap model and a threshold of 0.2319.

| | Predicted | NTBT (0) | TBT (1) |
|---|---|---|---|
| Observed | NTBT (0) | 53 | 63 |
| | TBT (1) | 9 | 86 |

TABLE 7c

Contingency table of TBT/NTBT patients observed and predicted by the bootstrap model and a threshold of 0.6465.

| | Predicted | NTBT (0) | TBT (1) |
|---|---|---|---|
| Observed | NTBT (0) | 105 | 11 |
| | TBT (1) | 45 | 50 |

Comparison to Other NASH Scoring Methods

Methods to establish NASH scores were previously described in literature:
  the Angulo Index (Angulo et al, 2007)
  ELF (Guha et al, 2008) (see also the ELF specification sheet http://www.healthcare.siemens.com/clinical-specialities/liver-disease/elf-test-now-avail)
  Fibrotest (Ratziu et al, 2006)
  Fibrometer (Cales et al, 2009)
  FLI (Bedogni et al, 2006)
  Steatosis Grade or SteatoTest (Poynard et al, 2005)

Figure 1A:
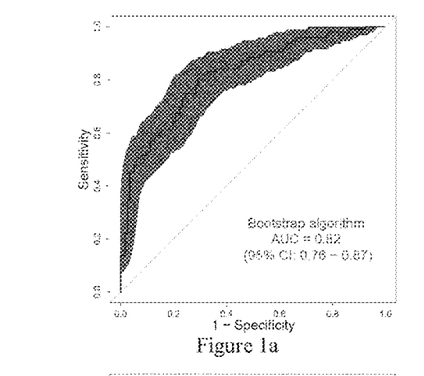
FIGS. 1a to 1g show comparison of the NASH scoring according to the method of the invention derived from the Bootstrap model (FIG. 1a) with existing scores.
Figure 1B:
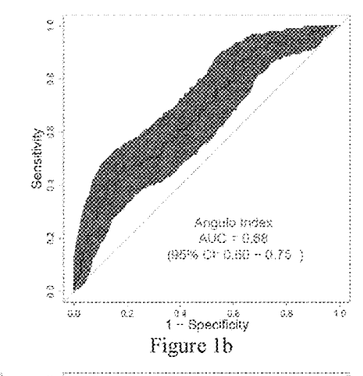
Figure 1C:
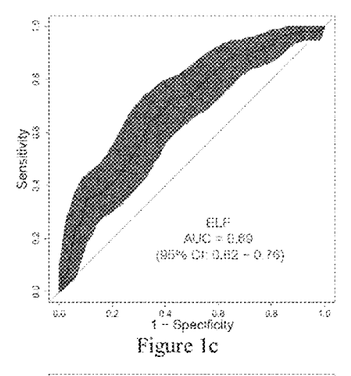
Figure 1D:
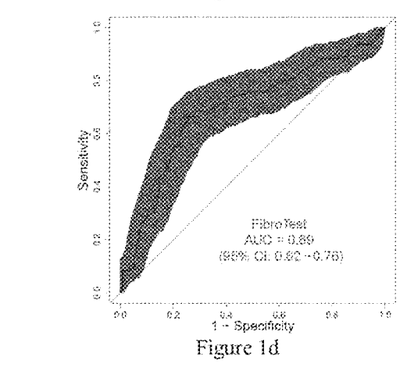
Figure 1E:
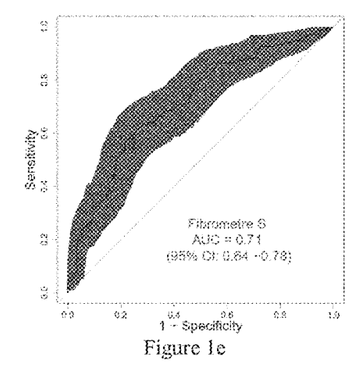
Figure 1F:
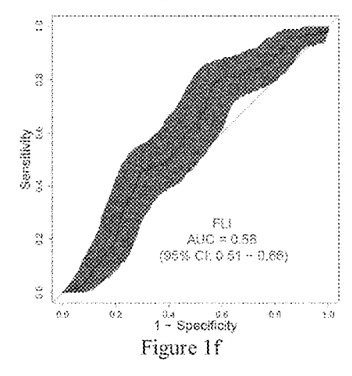
Figure 1G:
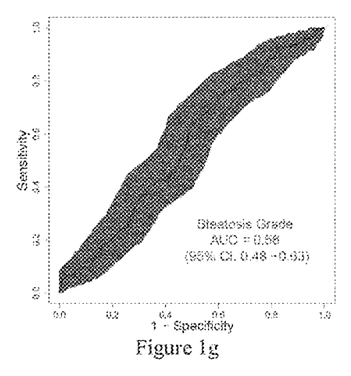

The inventors thus evaluated the NASH score of the invention to a number of these previous methods. FIGS. 1a to 1g show comparison of the NASH scoring according to the method of the invention derived from the Bootstrap model (FIG. 1a) with existing scores.

The data presented herein show a spectacular improvement of the accuracy of the identification of NASH patients, or potential NASH patients, determination of NASH activity, stage or severity. This finding is of outmost importance and will be an invaluable tool to improve patient management efficiency.

Further Objects Disclosed Herein

The present disclosure relates in particular to the following objects:

1. A method for the diagnosis of non-alcoholic steatohepatitis (NASH) or for determining the activity, the stage, or the severity of NASH in a subject, comprising the measure of the level of at least one blood, serum or plasma circulating micro-RNA marker of NASH and at least one other blood, serum or plasma circulating marker of liver damage.
2. The method according to object 1, comprising the step of measuring the level of at least one marker selected from either group (i), (ii) or (iii), and at least one marker selected from either group (iv) or (v) defined as follows:
   (i) alpha 2 macroglobulin
   (ii) glycated haemoglobin (HbA1c), fasting glucose level, fructosamine level
   (iii) N-terminal pro-peptide of collagen type III
   (iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
   (v) hsa-miR-200 (in particular hsa-miR-200a, more particularly hsa-miR-200a-3p).
3. The method according to object 1 or 2, comprising the implementation of the following measures from a blood, serum or plasma sample of said subject:
   (i) determining the level of alpha 2 macroglobulin;
   (ii) determining the level of at least one marker selected in the group consisting of HbA1c, fasting glucose level, fructosamine level;
   (iii) determining the level of N-terminal pro-peptide of collagen type III;
   (iv) determining the level of at least one marker selected in the group consisting of hsa-miR-34, hsa-miR-122 and hsa-miR-192; and
   (v) determining the level of hsa-miR-200;

wherein an increase in said levels relative to that of a control sample is indicative of NASH and/or of the activity, the stage, or the severity of NASH.

4. The method according to object 2 to 3, wherein:
   measure (ii) comprises determining the level of at least HbA1c; and/or
   measure (iv) comprises determining the level of at least hsa-miR-34.

5. The method according to any one of objects 1 or 4, comprising determining the level of alpha 2 macroglobulin, HbA1c, N-terminal pro-peptide of collagen type III, hsa-miR-34 and hsa-miR-200.

6. The method according to any one of objects 2 to 5, wherein a NASH score is calculated from the levels determined in measures (i) to (v) and wherein NASH is diagnosed and/or NASH stage or activity or severity is determined on the basis of said NASH score.

7. The method according to object 6, wherein a NASH score is calculated according to the following logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.

8. The method according to object 7, wherein:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.

9. The method according to object 7 or 8, wherein a NASH score higher than a threshold value
comprised between 0.102 and 0.6465 is indicative of a severe NASH, or of a moderate or high NASH activity.

10. The method according to object 9, wherein:
k is equal to 25.13;
a is equal to 0.60;
b is equal to 0.48;
c is equal to 0.1;
d is equal to −0.43; and
f is equal to −0.45;
and wherein the threshold value is comprised between 0.102 and 0.462, and is more particularly equal to 0.23.

11. The method according to object 9, wherein:
k is equal to 21.35;
a is equal to 0.62;
b is equal to 0.55;
c is equal to 0.14;
d is equal to −0.38; and
f is equal to −0.39;
and wherein the threshold value is comprised between 0.2319 and 0.6465, and is more particularly equal to 0.4343

12. A method for classifying a subject as a receiver or non receiver of a treatment for non-alcoholic steatohepatitis (NASH), comprising the measure of the level of at least one blood, serum or plasma circulating micro-RNA marker of NASH and at least one other blood, serum or plasma circulating marker of liver damage.

13. The method according to object 12, comprising the step of measuring the level of at least one marker selected from either group (i), (ii) or (iii), and at least one marker selected from either group (iv) or (v) defined as follows:
   (i) alpha 2 macroglobulin
   (ii) glycated haemoglobin (HbA1c), fasting glucose level, fructosamine level
   (iii) N-terminal pro-peptide of collagen type III
   (iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
   (v) hsa-miR-200 (in particular hsa-miR-200a, more particularly hsa-miR-200a-3p).

14. The method according to object 12 or 13, comprising the implementation of the following measures from a blood, serum or plasma sample of said subject:
   (i) determining the level of alpha 2 macroglobulin;
   (ii) determining the level of at least one marker selected in the group consisting of HbA1c, fasting glucose level, fructosamine level;
   (iii) determining the level of N-terminal pro-peptide of collagen type III;
   (iv) determining the level of at least one marker selected in the group consisting of hsa-miR-34, hsa-miR-122 and hsa-miR-192; and
   (v) determining the level of hsa-miR-200;
wherein a NASH score is calculated from the levels determined in measures (i) to (v) and wherein the subject is classified as a receiver or non receiver of the treatment for NASH based on said score.

15. The method according to object 13 or 14, wherein:
   measure (ii) comprises determining the level of at least HbA1c; and/or
   measure (iv) comprises determining the level of at least hsa-miR-34.

16. The method according to any one of objects 13 to 15, comprising determining the level of alpha 2 macroglobulin, HbA1c, N-terminal pro-peptide of collagen type III, hsa-miR-34 and hsa-miR-200.

17. The method according to object 16, wherein the NASH score is calculated according to the following logistic function:

$$S = \frac{e^Y}{1+e^Y}$$

wherein:

$$Y = k + a*A + b*B + c*C + d*D + f*F$$

wherein:
S is the NASH score;
A is the level of alpha 2 macroglobulin in g/L;
B is the level of HbA1c in percent;

C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.
18. The method according to object 17, wherein:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04.
19. The method according to any one of objects 17 or 18, wherein the subject is classified as a receiver of the treatment if S is higher than a threshold value comprised between 0.102 and 0.6465.
20. The method according to object 19, wherein:
k is equal to 25.13;
a is equal to 0.6;
b is equal to 0.48;
c is equal to 0.1;
d is equal to −0.43; and
f is equal to −0.45;
and wherein the threshold value is comprised between 0.102 and 0.462, and is more particularly equal to 0.23.
21. The method according to object 19, wherein:
k is equal to 21.35;
a is equal to 0.62;
b is equal to 0.55;
c is equal to 0.14;
d is equal to −0.38; and
f is equal to −0.39;
and wherein the threshold value is comprised between 0.2319 and 0.6465, and is more particularly equal to 0.4343.
22. A method for calculating a NASH score which is indicative of non-alcoholic steatohepatitis (NASH), or of the activity, the stage, or the severity of NASH in a subject, wherein said score is based on the measure of at least one marker selected from either group (i), (ii) or (iii), and at least one marker selected from either group (iv) or (v) defined as follows:
  (i) alpha 2 macroglobulin
  (ii) glycated haemoglobin (HbA1c), fasting glucose level, fructosamine level
  (iii) N-terminal pro-peptide of collagen type III
  (iv) hsa-miR-34 (in particular hsa-miR-34a, more particularly hsa-miR-34a-5p), hsa-miR-122 (in particular hsa-miR-122-5p) and hsa-miR-192 (in particular hsa-miR-192-5p)
  (v) hsa-miR-200 (in particular hsa-miR-200a, more particularly hsa-miR-200a-3p).
23. The method according to object 22, wherein the following (i) to (v) measures are determined from a blood, serum or plasma sample of said subject:
  (i) the level of alpha 2 macroglobulin;
  (ii) the level of at least one marker selected in the group consisting of HbA1c, fasting glucose level, fructosamine level;
  (iii) the level of N-terminal pro-peptide of collagen type III;
  (iv) the level of at least one marker selected in the group consisting of hsa-miR-34, hsa-miR-122 and hsa-miR-192; and
  (v) the level of hsa-miR-200.
24. The method of object 23, comprising determining the level of alpha 2 macroglobulin, HbA1c, N-terminal pro-peptide of collagen type III, hsa-miR-34 and hsa-miR-200.
25. The method of object 24, wherein the NASH score is calculated according to the following logistic function:

$$S = \frac{e^Y}{1+e^Y}$$

wherein:

$$Y=k+a*A+b*B+c*C+d*D+f*F$$

wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34 in Cq;
F is the level of hsa-miR-200 in Cq;
k is a number comprised between 5.26 and 36.76;
a is a number comprised between 0.11 and 1.07;
b is a number comprised between 0 and 1.02;
c is a number comprised between 0 and 0.23;
d is a number comprised between −0.77 and 0;
f is a number comprised between −0.78 and 0.
26. The method according to object 25, wherein:
k is a number comprised between 5.26 and 36.76;
a is a number comprised between 0.11 and 1.07;
b is a number comprised between 0.001 and 1.02;
c is a number comprised between 0.001 and 0.23;
d is a number comprised between −0.77 and −0.001;
f is a number comprised between −0.78 and −0.04
27. The method according to object 25, wherein:
k is equal to 25.13;
a is equal to 0.6;
b is equal to 0.48;
c is equal to 0.1;
d is equal to −0.43; and
f is equal to −0.45.
28. The method according to object 25, wherein:
k is equal to 21.35;
a is equal to 0.62;
b is equal to 0.55;
cis equal to 0.14;
d is equal to −0.38; and
f is equal to −0.39.
29. A kit comprising means for determining the level of:
  (i) alpha 2 macroglobulin;
  (ii) at least one marker selected in the group consisting of HbA1c, fasting glucose level, fructosamine level;
  (iii) N-terminal pro-peptide of collagen type III;
  (iv) at least one marker selected in the group consisting of has-miR-34, hsa-miR-122 and hsa-miR-192; and
  (v) hsa-miR-200.
30. The kit according to object 29, comprising means for determining the level of alpha 2 macroglobulin, HbA1c, N-terminal pro-peptide of collagen type III, hsa-miR-34 and hsa-miR-200.

31. A method for treating non-alcoholic steatohepatitis (NASH) in a subject, comprising:
(a) diagnosing NASH or determining the activity, the stage, or the severity of NASH in a subject according to the method of any one of objects 1 to 11;
(b) administering a treatment for NASH to said subject based on step (a).

32. A method for treating non-alcoholic steatohepatitis (NASH) in a subject, comprising:
(a) classifying said subject according to the method of any one of objects 12 to 21;
(b) administering a treatment for NASH to the subject if said subject is classified as receiver of the treatment according to step (a).

33. The method according to object 31 or 32, wherein the treatment comprises administering to the subject a compound of formula (I):

wherein:
X1 represents a halogen, a R1, or G1-R1 group;
A represents a CH=CH or a CH2-CH2 group;
X2 represents a G2-R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups;
or a pharmaceutically acceptable salt thereof.

34. The method according to object 33, wherein the compound is selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyloxyphenyl]prop-2-en-1-one, 2-[2,6-dimethyl-4-[3-[4-(methylthio)phenyl]-3-oxo-propyl]phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester; or a pharmaceutically acceptable salt thereof.

35. The method according to object 33 or 34, wherein the compound is 1-[4-methylthiophenyl]-3-[3,5-dimethyl-4-carboxydimethylmethyloxy phenyl]prop-2-en-1-one or a pharmaceutically acceptable salt thereof.

36. The method according to object 31 or 32, wherein the treatment comprises administering to the subject a compound of Table 1.

REFERENCES

Angulo P, Hui J M, Marchesini G, Bugianesi E, George J, Farrell G C, Enders F, Saksena S, Burt A D, Bida J P, Lindor K, Sanderson S O, Lenzi M, Adams L A, Kench J, Therneau T M, Day C P (2007) The NAFLD fibrosis score: a noninvasive system that identifies liver fibrosis in patients with NAFLD. *Hepatology* 45: 846-854

Bedogni G, Bellentani S, Miglioli L, Masutti F, Passalacqua M, Castiglione A, Tiribelli C (2006) The Fatty Liver Index: a simple and accurate predictor of hepatic steatosis in the general population. *BMC Gastroenterol* 6: 33

Cales P, Laine F, Boursier J, Deugnier Y, Moal V, Oberti F, Hunault G, Rousselet M C, Hubert I, Laafi J, Ducluzeaux P H, Lunel F (2009) Comparison of blood tests for liver fibrosis specific or not to NAFLD. *J Hepatol* 50: 165-173

Guha I N, Parkes J, Roderick P, Chattopadhyay D, Cross R, Harris S, Kaye P, Burt A D, Ryder S D, Aithal G P, Day C P, Rosenberg W M (2008) Noninvasive markers of fibrosis in nonalcoholic fatty liver disease: Validating the European Liver Fibrosis Panel and exploring simple markers. *Hepatology* 47: 455-460

Poynard T, Ratziu V, Naveau S, Thabut D, Charlotte F, Messous D, Capron D, Abella A, Massard J, Ngo Y, Munteanu M, Mercadier A, Manns M, Albrecht J (2005) The diagnostic value of biomarkers (SteatoTest) for the prediction of liver steatosis. *Comp Hepatol* 4: 10

Ratziu V, Massard J, Charlotte F, Messous D, Imbert-Bismut F, Bonyhay L, Tahiri M, Munteanu M, Thabut D, Cadranel J F, Le Bail B, de Ledinghen V, Poynard T (2006) Diagnostic value of biochemical markers (FibroTest-FibroSURE) for the prediction of liver fibrosis in patients with non-alcoholic fatty liver disease. *BMC Gastroenterol* 6: 6

The invention claimed is:

1. A method for treating non-alcoholic steatohepatitis (NASH) in a subject, comprising:
(a) diagnosing NASH or determining the activity, the stage, or the severity of NASH in a subject according to a process comprising the step of measuring in a blood, serum or plasma sample the level of biomarkers consisting of:
(i) alpha 2 macroglobulin,
(ii) glycated haemoglobin (HbA1c),
(iii) N-terminal pro-peptide of collagen type III,
(iv) hsa-miR-34a-5p,
(v) hsa-miR-200a-3p;
wherein an increase in each level of the biomarkers relative to that of a control sample is indicative of NASH and/or of the activity, the stage, or the severity of NASH, and
(b) performing a treatment for NASH to said subject based on step (a) wherein the treatment comprises administering to the subject a compound of formula (I):

or a pharmaceutically acceptable salt thereof;
wherein:
X1 represents a halogen, a R1, or G1-R1 group;
A represents a CH=CH or a CH2-CH2 group;
X2 represents a G2-R2 group;
G1 represents an atom of oxygen;
G2 represents an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is unsubstituted or substituted by one or more halogen atoms, cycloalkyl groups, or heterocyclic groups; and
R4 and R5, identical or different, representing an alkyl group that is unsubstituted or substituted by one or more halogen atoms, cycloalkyl groups, and heterocyclic groups.

2. A method for treating non-alcoholic steatohepatitis (NASH) in a subject, comprising:
(a) classifying a subject as a receiver or non-receiver of a treatment for non-alcoholic steatohepatitis (NASH), according to a process comprising the step of measuring in a blood, serum or plasma sample the level of biomarkers consisting of:
(i) alpha 2 macroglobulin,
(ii) glycated haemoglobin (HbA1c),
(iii) N-terminal pro-peptide of collagen type III,
(iv) hsa-miR-34a-5p, and
(v) hsa-miR-200a-3p;
wherein an increase in each level of the biomarkers relative to that of a control sample is indicative of NASH and/or of the activity, the stage, or the severity of NASH, and
(b) performing the treatment for NASH to said subject based on step (a) wherein the treatment comprises administering to the subject a compound of formula (I):

or a pharmaceutically acceptable salt thereof;
wherein:
X1 represents a halogen, a R1, or G1-R1 group;
A represents a CH=CH or a CH2-CH2 group;
X2 represents a G2-R2 group;
G1 represents an atom of oxygen;
G2 represents an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is unsubstituted or substituted by one or more halogen atoms, cycloalkyl groups, or heterocyclic groups; and
R4 and R5, identical or different, representing an alkyl group that is unsubstituted or substituted by one or more halogen atoms, cycloalkyl groups, and heterocyclic groups.

* * * * *

SEQUENCE LISTING

<160> NUMBER OF SEQ ID NOS: 10

<210> SEQ ID NO 1
<211> LENGTH: 22
<212> TYPE: RNA
<213> ORGANISM: Caenorhabditis elegans

<400> SEQUENCE: 1
ucaccggguc uaaaucagcu ug                                          22

<210> SEQ ID NO 2
<211> LENGTH: 22
<212> TYPE: RNA
<213> ORGANISM: homo sapiens

<400> SEQUENCE: 2
uggaguguga caauggucuu ug                                          22

<210> SEQ ID NO 3
<211> LENGTH: 22
<212> TYPE: RNA
<213> ORGANISM: homo sapiens

<400> SEQUENCE: 3
uggcaguguc uuagcugguu gu                                          22

<210> SEQ ID NO 4
<211> LENGTH: 22
<212> TYPE: RNA
<213> ORGANISM: homo sapiens

<400> SEQUENCE: 4
uaacacuguc ugguaacgau gu                                          22

<210> SEQ ID NO 5
<211> LENGTH: 23
<212> TYPE: RNA
<213> ORGANISM: homo sapiens

<400> SEQUENCE: 5
uagcaccauu ugaaaucagu guu                                         23

<210> SEQ ID NO 6
<211> LENGTH: 21
<212> TYPE: RNA
<213> ORGANISM: homo sapiens

<400> SEQUENCE: 6
cugaccuaug aauugacagc c                                           21

<210> SEQ ID NO 7
<211> LENGTH: 23
<212> TYPE: RNA
<213> ORGANISM: homo sapiens

<400> SEQUENCE: 7
agcuacauug ucugcugggu uuc                                         23

<210> SEQ ID NO 8
<211> LENGTH: 23
<212> TYPE: RNA
<213> ORGANISM: homo sapiens

<400> SEQUENCE: 8
agcagcauug uacagggcua uga                                         23

<210> SEQ ID NO 9
<211> LENGTH: 23
<212> TYPE: RNA
<213> ORGANISM: homo sapiens

<400> SEQUENCE: 9

```
uuaaugcuaa ucgugauagg ggu                                    23

<210> SEQ ID NO 10
<211> LENGTH: 23
<212> TYPE: RNA
<213> ORGANISM: homo sapiens

<400> SEQUENCE: 10
cccaguguuc agacuaccug uuc                                    23
```